United States Patent
Yang et al.

(10) Patent No.: US 8,680,087 B2
(45) Date of Patent: Mar. 25, 2014

(54) MACROCYCLIC AMIDES, PHARMACEUTICAL COMPOSITIONS, PREPARATION METHODS AND USES THEREOF

(75) Inventors: Chongren Yang, Yuxi (CN); Haizhou Li, Yuxi (CN); Ping Zhao, Yuxi (CN); Yingjun Zhang, Yuxi (CN)

(73) Assignee: Yuxi Winhey Bio-Tech Co., Ltd. (CN)

( * ) Notice: Subject to any disclaimer, the term of this patent is extended or adjusted under 35 U.S.C. 154(b) by 0 days.

(21) Appl. No.: 13/512,672

(22) PCT Filed: Nov. 30, 2010

(86) PCT No.: PCT/CN2010/001928
§ 371 (c)(1),
(2), (4) Date: May 30, 2012

(87) PCT Pub. No.: WO2011/063615
PCT Pub. Date: Jun. 3, 2011

(65) Prior Publication Data
US 2012/0238538 A1    Sep. 20, 2012

(30) Foreign Application Priority Data

Nov. 30, 2009 (CN) .......................... 2009 1 0218257

(51) Int. Cl.
*C07D 225/02* (2006.01)
*A61K 31/395* (2006.01)
*A61P 35/00* (2006.01)

(52) U.S. Cl.
USPC .......................................... 514/183; 540/463

(58) Field of Classification Search
USPC .......................................... 540/463; 514/183
See application file for complete search history.

(56) References Cited

FOREIGN PATENT DOCUMENTS

| CN | 101735149 A | 6/2010 |
|---|---|---|
| WO | 2008143730 A2 | 11/2008 |

OTHER PUBLICATIONS

G. Furgani, E. Böszörményi, A. Fodor, A. Máthé-Fodor, S. Forst, J.S. Hogan, Z. Katona, M.G. Klein, E. Stackebrandt, A. Szentirmai, F. Sztaricskai, S.L. Wolf. *Xenorhabdus* antibiotics: A comparative analysis and potential utility for controlling mastitis caused by bacteria. Journal of Applied Microbiology, 2008, 104(3):745-758.
D. Ji, Y. Yi, G. Kang, Y. Choi, P. Kim, N. Baek, Y. Kim. Identification of an antibacterial compound, benzylideneacetone, from *Xenorhabdus nematophila* against major plant-pathogenic bacteria. FEMS Microbiology Letters, 2004, 239(2):241-248.
G. Lang, T. Kalvelage, A. Peters, J. Wiese, J.F. Imhoff. Linear and cyclic peptides from the entomopathogenic bacterium *Xenorhabdus nematophilus*. Journal of Natural Products, 2008, 71(6):1074-1077.
Skehan, et al. (1990) J.-X. Li, G.-H. Chen, J.M. Webster. Nematophin, A novel antimicrobial substance produced by *Xenorhabdus nematophilus* (Enterobactereaceae). Canadian Journal of Microbiology, 1997, 43(8): 770-773.
Liu Wei-jing, Yang Xiu-fen, Jian Hen, LV Qiu-jun, Dong Jun-xing. The anti-tumor activity of metabolites from *Xenorhabdus* and *Photorhabdus* in vitro. Natural Product Research and Development, 2004, 16(1): 1-6. (in Chinese), (English Abstract).
S. Park, Y.H. Park, S. Suh, H.S. Kim, I.S. Lee, M.K. Park, C.S. Lee, S.H. Park. Unusual cytotoxic phenethylamides from *Xenorhabdus nematophilus*. Bulletin of the Korean Chemical Society, 2001, 22(4):372-374.
International Search Report for International Application No. PCT/CN2010/001928, mailed Mar. 10, 2011, with English translation.

*Primary Examiner* — Bruck Kifle
(74) *Attorney, Agent, or Firm* — Cantor Colburn LLP

(57) ABSTRACT

Macrocyclic amide WH-21091 with antibacterial and antitumor activities, its analogs, preparation methods and uses thereof. The said macrocyclic amides are prepared by microbes of *Xenorhabdus* and *Photorhabdus*, or they can be prepared by other living beings through transgenic techniques. The compositions of the said macrocyclic amide and its analogs can be used as drugs and/or agricultural chemicals for treatment of microbial infections, especially for treatment of infectious diseases of *Staphylococcus aureus* with drug resistance. The said compositions can also be used as drugs for treatment of cancers of human beings or animals.

10 Claims, No Drawings

MACROCYCLIC AMIDES, PHARMACEUTICAL COMPOSITIONS, PREPARATION METHODS AND USES THEREOF

CROSS REFERENCE TO RELATED APPLICATIONS

This is a U.S. national stage of application No. PCT/CN2010/001928, filed on 30 Nov. 2009. Priority under 35 U.S.C. §119(a) and 35 U.S.C. §365(b) is claimed from Japanese Application No. 200910218257.3, filed 30 Nov. 2009, the disclosure of which are also incorporated herein by reference.

TECHNICAL FIELD

The present invention relates to the technical field of biopharmaceuticals and specifically relates to a novel macrocyclic amide with antibacterial and antitumor activities, and its analog, composition, preparation method and use.

BACKGROUND OF THE ART

Along with the development of the society and the economy, changing of the living environment and the living habits of the human being, new diseases keep emerging, the diseases controlled by synthetic drugs reoccur and become more severe. Meanwhile, the abuses of antibiotics cause drug tolerance of pathogenic bacteria, resulting in that normal dosage of drugs is insufficient to exert the antibacterial effects as expected. In addition, malignant tumor has become one of the main causes of death, which severely threatens the health and life of the human being. The spreading of the diseases causes new disasters to the human being. In the aspect of agroforestry, the humans are facing the challenges of the tolerance of the pathogenic bacteria to bactericides and chemical pesticides. Therefore, continuous development of new and effective drugs has drawn great attentions. There are a great deal of microbes in the soil, including bacteria, fungi, actinomycetes, virus, protista, and the like. The molecular diversity of the secondary metabolic products of soil microbes is the resource of the research and development of new drugs and new pesticides.

Symbiotic bacteria of entomogenous nematodes in the soil produce secondary metabolic products having physiological activities, such as antibacterial substances, insecticidal proteins, extracellular enzymes, and the like. One of the common features of symbiotic bacteria is the production of antibiotics, which has a broad commercial prospect as an antibacterial substance for inhibiting the growth of bacteria, fungi and yeasts (Webster et al., 2002).

A great deal of research has indicated that the metabolic products of gram negative bacteria such as species of Enterobacteriaceae *Xenorhabdus* and *Photorhabdus*, which are symbiotic with *Steinernema* and *Heterorhabditis* nematodes, can not only inhibit the growth of various bacteria and fungi, but also show pesticidal activities and activities for inhibiting the growth of tumor cells. Therefore, it has become interested by scientists from home and abroad to seek physiologically active substances from this type of specifically habitated bacteria (Li, 1997; Park, 2001; LIU Wei Jing, 2004; Furgani, 2008). Currently, new antibacterial substances have been discovered from their metabolic products, such as xenocoumacins, nematophin (Li, 1997, 1998), xenorxides (Li, 1998), benzylineacetone (Ji, 2004), xenorxides and xenematide (Lang, 2008), etc. Xenorxides also showed significant antitumor activities.

SUMMARY OF THE INVENTION

The present invention provides a macrocyclic amide WH-21091 (named by the inventors), and an analog, pharmaceutically acceptable salt, solvate, polymorph, ester, tautomer or prodrug thereof. The present invention also provides a method for preparing the macrocyclic amide and use thereof, as well as a pharmaceutical composition comprising any of the above. The macrocyclic amide and an analog, pharmaceutically acceptable salt, solvate, polymorph, ester, tautomer or prodrug thereof show antibacterial and antitumor activities, and can be used to treat or prevent diseases such as infection and cancer.

According to one aspect, the present invention provides a macrocyclic amide WH-21091, or a pharmaceutically acceptable salt, solvate, polymorph, ester, tautomer or prodrug thereof, wherein the macrocyclic amide WH-21091 has a structure of formula I:

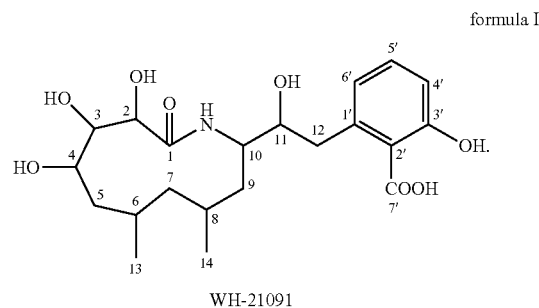 [SMILES: CC1CC(C)CC(C(O)Cc2cccc(O)c2C(=O)O)NC(=O)C(O)C(O)C(O)C1]

formula I

WH-21091

According to another aspect, the present invention provides an analog, or a pharmaceutically acceptable salt, solvate, polymorph, ester, tautomer or prodrug of a macrocyclic amide WH-21091, having a structure represented by formula II:

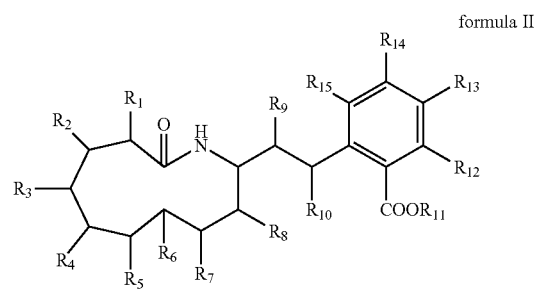

formula II wherein, one or more of $R_1$-$R_{15}$ may independently be hydrogen atom, or alkyl, cycloalkyl, alkenyl, alkynyl, aromatic group, or a group containing one or more of oxygen, nitrogen, sulfur or halogen, or a heterocyclic group, wherein the group containing oxygen includes hydroxyl, acyl, ketone group, and carboxyl, and the group contain nitrogen includes amino and nitro.

In an embodiment, each of $R_1$-$R_3$, $R_9$ and $R_{12}$ is independently a group containing one or more of oxygen, nitrogen, sulfur or halogen atoms such as hydroxyl, alkoxy (for example, $C_{1-6}$ alkoxy) and thioalkyl (for example, $C_{1-6}$ thioalkyl); and each of $R_4$-$R_8$, $R_{10}$-$R_{11}$ and $R_{13}$-$R_{14}$ is independently selected from hydrogen, $C_{1-6}$ alkyl (preferably $C_{1-4}$ alkyl), $C_{2-6}$ alkenyl (preferably $C_{2-4}$ alkenyl), and $C_{2-6}$ alkynyl (preferably $C_{2-4}$ alkynyl).

According to another aspect, the present invention provides a method for preparing the macrocyclic amide WH-21091. The macrocyclic amide WH-21091 is a secondary metabolic product of microbes including, but not limited to, parasitic bacilli of *Xenorhabdus*, such as *Xenorhabdus bovienii, X. nematophila, X. ehlersii* and *X. budapestensis*, etc., and *Photorhabdus*, which parasitize in *Steinernema* and *Heterorhabditis* nematodes and are symbiotic therewith. The macrocyclic amide may be obtained by isolation from the secondary metabolic products of the above microbes.

The method for preparing the macrocyclic amide WH-21091 may be, for example:

1) infecting last-instar larvae of *Galleria mellonella* with nematodes larvae of parasitic bacilli; disinfecting and anatomizing dead larvae; taking lymph and placing on agar medium and culturing at room temperature in dark; and isolating bacilli;
2) culturing of bacilli: the above bacilli are cultured for fermentation, inoculated in a liquid medium containing a carbon source and a nitrogen source, aerobically cultured at 23-27° C. for 24-96 hours, during which the antibacterial activity of the medium is determined at certain intervals until the antibacterial activity of WH-21091 is produced in the medium. When the strains are cultured in a liquid medium containing a carbon source and a nitrogen source, a primary culture is conducted firstly, followed by a secondary culture;
3) preparing WH-21091: after the fermentation culture, the thalli are removed through filtration or centrifuge; the clear solution is adjusted with acetic acid to a pH of 7.0, and extracted with chloroform or ethyl acetate, the extracted solutions are combined, filtered, and concentrated under reduced pressure at 40-50° C.; the obtained extract is separated with column chromatography and eluted with solvent gradient to obtain the macrocyclic amide WH-21091 with antibacterial activities. The separation and purification process is monitored by thin-layer chromatography and antibacterial activity determination. The separation and purification may also be conducted with high-pressure liquid chromatography. When the separation is conducted with column chromatography, the stationary phase may be any of silica gel, resin or gel. When silica gel column chromatography is used, the silica gel is 200-300 mesh silica gel for column chromatography, and the ratio of the extract to the silica gel is 1:15. When the secondary metabolic products produced by bacilli are separated and purified with chromatography, and chloroform and methanol or petroleum ether or acetone or mixtures thereof may be used as the eluent.

The macrocyclic amide WH-21091 may also be produced by other organisms through a transgenic method, which comprises: manually isolating a target gene producing WH-21091, modifying said gene and incorporating into the genome of other organisms including *Escherichia coli* through linkage to a vector. The expression of the introduced gene leads to hereditable modification of the characters of the organisms, thereby producing WH-21091.

The compound of formula II of the present invention may be obtained by modification of the structure of the compound of formula I. For example, the compound of formula II may be obtained by modification of the structure of the compound of formula I with conventional methods in the art, such as those disclosed in *Comprehensive Organic Synthesis*, By B. M. Trost, I. Fleming; Publisher: Pergamon, Publication Date: Dec. 1, 1991.

According to another aspect, the present invention provides a use of the compound of formula I or II or a pharmaceutically acceptable salt, solvate, polymorph, ester, tautomer or prodrug thereof in the manufacture of a medicament. Preferably, the medicament is a medicament for treating or preventing infections or an antitumor medicament for treating or preventing cancers.

According to another aspect, the present invention relates to a method for treating diseases, conditions or disorders in a mammal, comprising administrating to the mammal a therapeutically effective amount of the compound of formula I or II or a pharmaceutically acceptable salt, solvate, polymorph, ester, tautomer or prodrug thereof. The mammal is preferably human.

According to an embodiment of the present invention, the diseases, conditions or disorders described in the present invention include for example infections caused by bacteria, cancers, and the like.

The compound of formula I or II of the present invention, or a pharmaceutically acceptable salt, solvate, polymorph, ester, tautomer or prodrug thereof shows significant antibacterial activities to most of gram positive pathogenic bacteria and fungi. Specially, for the infections caused by drug-tolerant bacteria (such as drug-tolerant *Staphylococcus aureus*, etc.), it shows higher activities than the common antibiotics commercially available. It can be used in treating and preventing the infections caused by these pathogenic bacteria, and is a new generation of broad-spectrum antibiotics for replacing the currently used ones. The subject can be treated includes plants and animals, including mammals such as dog, cat and other domestic animals, especially human. For example, it can inhibit bacteria of such as *Escherichia, Staphylococcus, Enterococcus, Streptococcus, Pseudomonas*.

The compound of formula I or II of the present invention, or a pharmaceutically acceptable salt, solvate, polymorph, ester, tautomer or prodrug thereof shows antitumor activities, and can inhibit the growth of cancer cells. For example, it may be used for preventing or treating brain cancer, breast cancer, cervix cancer, lung cancer, ovary cancer, pancreatic cancer, prostate cancer, kidney cancer, colorectal cancer or leukemia.

The formulation, administration manner route and dosage of the compound of the present invention, or a pharmaceutically acceptable salt, solvate, polymorph, ester, tautomer or prodrug thereof may be selected by a person skilled in the art. Exemplary dosage for adults may be from about 2.000 mg to about 2.5 mg per day. The administration to mammals may be implemented orally, parenterally or topically, and the administration to plant subjects may be implemented by applying to the seed, the leaf, or other parts of the plant, or into the soil.

The compound of the present invention, or a pharmaceutically acceptable salt, solvate, polymorph, ester, tautomer or prodrug thereof may be used alone or as a pharmaceutically acceptable formulation, which contains one or more conventional carriers in addition to the active ingredient. Depending on the nature of the disease to be treated and/or the administration route, the compound of the present invention may be formulated by methods known in the art.

According to another aspect, the present invention provides a pharmaceutical composition comprising the compound of formula I or II, or a pharmaceutically acceptable salt, solvate, polymorph, ester, tautomer, prodrug thereof and one or more pharmaceutically acceptable carriers or excipient. The forms of the pharmaceutical composition include any solid formulation (tablet, pill, capsule, granule, powder, etc.) or liquid formulation (solution, suspension or emulsion) suitable for oral, topical or parenteral administration. They may comprise only the compound of formula I or II of the present invention, or a pharmaceutically acceptable salt, solvate, polymorph, ester, tautomer, prodrug thereof, or may be combined with any pharmaceutically acceptable carrier or excipient or other pharmaceutically active compounds. When administered parenterally, the formulation is required to be prepared under sterilization.

The administered dosage depends on the type of the disease, the type of the subject (including the age, health condition and body weight thereof), concurrently conducted other treatments (if any), as well as the frequency of the treatment and therapeutic ratio, and the dosage level of the active ingredient used, and may be 0.1 to about 200 mg/kg body weight of the subject when intravenously administered; 1 to about 500 mg/kg body weight of the subject when intramuscularly administered; 5 to about 1000 mg/kg body weight of the subject when orally administered; 5 to about 1000 mg/kg body weight of the subject when intranasally administered; and 5 to about 1000 mg/kg body weight of the subject when administered as sprays. When expressed with concentration, the concentration of the compound of the present invention may be about 0.01 to about 50% (w/w), preferably about 1 to about 20% (w/w) when it is topically administered to the skin, the nasal cavity, the throat, the bronchus, the vagina, the recta, or the eye. Similarly, for parenteral administration, the concentration employed may be about 0.05 to about 50% (w/w), preferably about 5 to about 20% (w/w). In the treatment of diseases in animals and humans, the compound of the present invention or a pharmaceutically acceptable salt, solvate, polymorph, ester, tautomer or prodrug thereof, as an active ingredient of an antibacterial agent and/or an antitumor agent, may be easily formulated into unit dosage forms with pharmaceutically acceptable materials and well-developed technologies in the art. It can be prepared with methods known to a person skilled in the art by selecting suitable solid or liquid excipient or diluent.

For agricultural applications, the antibacterial compound, or a pharmaceutically acceptable salt, solvate, polymorph, ester, tautomer or prodrug thereof may be formulated in an inert carrier. When formulated into a solid, the active ingredient may be mixed with commonly used carriers such as bleaching clay, kaolin, kieselguhr, or other wettable smear diluents. Flowable powder formulations may also be used, which may be prepared by mixing dry active ingredient with fine solids such as talc powder, pyrophyllite, clay and kieselguhr.

Depending on its solubility in liquid carrier, the powder may be applied in a form of suspension or solution. Pressurized spray may also be used, especially spray containing active ingredients dispersed in a low-boiling-point dispersing solvent carrier. The weight percentage of the compound may be adjusted depending on the application manner of the compound and the formulation used. Normally, the antibacterial formulation may contain 0.005 wt % to 95 wt % of the active ingredient. The antibacterially active compound may be used in combination with other ingredients including growth regulation factors, pesticides, fertilizers, and the like, which facilitate the application and operation, maintain the chemical stability, and improve the efficacy. The solvent may be selected depending on the solubility, emulsifiability, specific gravity and economic factor of the active ingredient. Adjuvants may be added to improve the activity. Surfactants including anionic, cationic and non-ionic surfactants may also be added. Stabilizers and antifreezers may be added to extend the storage duration. Furthermore, synergists, binders, spreaders and deodorizers may be added to improve the handling characteristics of commercial formulations. The active ingredient may be formulated into pills in combination with inert carriers such as calcium carbonate, or formulated into other consumable administration device, including controlled release administration device for quantitatively delivering the active ingredient.

The compound of the present invention, or a pharmaceutically acceptable salt, solvate, polymorph, ester, tautomer or prodrug thereof may also be used as an antibacterial agent for inhibiting the growth of the currently present microbes or eliminating the microbes on the surface of the living host or in the outer media of the living host. The compound of the present invention, or a pharmaceutically acceptable salt, solvate, polymorph, ester, tautomer or prodrug thereof may also be used as a disinfectant for disinfecting various solid or liquid media facilitating the growth of microbes. The suitable amount of the compound of the present invention may be determined with methods known by a person skilled in the art.

DEFINITIONS

The term "alkyl" used herein alone or in combination refers to optionally substituted linear or branched mono-valent saturated hydrocarbon having 1-10 carbon atoms, preferably 1-6 carbon atoms.

The term "alkenyl" used herein alone or in combination refers to optionally substituted linear or branched mono-valent hydrocarbon group having one or more C=C double bonds, and 2-10 carbon atoms, preferably 2 to about 6 carbon atoms. The double bonds in these groups may be trans- or cis-configuration, and shall be understood as including these isomers.

The term "alkynyl" used herein alone or in combination refers to optionally substituted linear or branched mono-valent hydrocarbon group having one or more C≡C triple bonds, and 2-10 carbon atoms, preferably 2-6 carbon atoms.

The term "aromatic group (or aryl)" used herein alone or in combination refers to optionally substituted aromatic hydrocarbon group having 6 to about 20 cyclic carbon atoms and including fused and non-fused aromatic rings. Fused aryl may contain 2-4 fused aromatic rings and other individual rings which may be aliphatic ring, hetero ring, aromatic ring, heteroaromatic ring, or any combination thereof. In addition, the term aromatic group includes fused and non-fused rings containing 6 to about 12 cyclic carbon atoms, and fused and non-fused rings containing 6 to about 10 cyclic carbon atoms.

The term "heterocyclyl" used herein alone or in combination collectively refers to aliphatic heterocyclyl and aromatic heterocyclyl. In the context of the present invention, when the number of the carbon atoms in a heterocyclyl is indicated (e.g. $C_1$-$C_6$ heterocyclyl), the heterocyclyl definitely contain at least one atom different from carbon (i.e. hetero atom). For example, the nomenclature of "$C_1$-$C_6$ heterocyclyl" indicates only the number of carbon atoms in the rings, not the total number of the atoms in the rings. The nomenclature of "4-6 membered heterocyclyl" refers to the total number of the atoms in the rings (i.e. 4-, 5- or 6-membered rings, wherein at least one atom is carbon, at least one atom is hetero atom, and the other 2-4 atoms may be carbon atom or hetero atom). For heterocyclyl having two or more hetero atoms, said two or more hetero atoms may the same or different from each other. The heterocyclyl may be optionally substituted.

The term "acyl" or "ketone group" used herein alone or in combination refers to R—C(O)—, wherein R is alkyl having 1-10 carbon atoms, preferably 1-6 carbon atoms.

The term "carboxyl" used herein alone or in combination refers to R—C(O)O—, wherein R is alkyl having 1-10 carbon atoms, preferably 1-6 carbon atoms.

The term "solvate" used herein refers to a combination of the compound of the present invention with a solvent molecule formed by solvation. Under certain circumstances, solvate refers to hydrate, i.e. the solvent molecule is a water molecule. The compound of the present invention combines with water to form a hydrate.

The term "polymorph" or "polymorphism" used herein refers to the compound of the present invention existing in different crystal lattice forms.

The term "ester" used herein refers to a derivative of the compound of the present invention derived from oxyacid group and hydroxyl group. The compound of the present invention may contain oxyacid group or hydroxyl group.

The term "tautomer" used herein refers to an isomer readily resulted from the compound of the present invention for example through hydrogen migration or proton migration.

The term "prodrug" used herein refers to any pharmaceutically acceptable salt, ester, salt of ester or other derivatives of the compound of the present invention, which, after being administered to a subject, can directly or indirectly provide the compound of the present invention or a pharmaceutically active metabolite or residue thereof. Specifically preferred prodrugs are those which can improve the bioavailability of the present invention when being administered to a patient (e.g. rendering the orally administered compound more readily absorbed into the blood), or those which can improve the delivery of the parent compound to organs or target sites (e.g. brain or lymphatic system).

EMBODIMENTS OF THE INVENTION

The following examples further illustrate the present invention, without limiting the present invention.

Example 1

Preparing and Isolating WH-21091 from Pathogenic *X. nematophila* Culture

*X. nematophilus* HB310 was used in this example.

The primary culture of the strains of the above *X. nematophilus* HB310 was maintained for 14 days, followed by secondary culture. Firstly, the primary culture was added into a 100 ml conical flask containing 50 ml of tryptic soy broth (TSB) medium with an inoculating loop, and the culture was continuously cultured in an Eberbach rotating oscillator under 25° C. and 120 rpm for 24 hours. 100 ml of this culture was inoculated into a 2000 ml flask containing 900 ml of TSB medium, and continuously cultured for fermentation in an Eberbach rotating oscillator under 25° C. and 120 rpm and dark conditions for 96 hours. The fermentation liquor was centrifuged under 4° C. and 12,000×g for 20 min to isolate the bacterial thalli. The thalli were further inoculated into 20 L of medium. The inoculated medium was cultured under 37° C. for 3 days. After culturing, the mixture is filtered or centrifuged to remove the thalli. The clear solution was adjusted with acetic acid to a pH of 7.0, and extracted with 20 L of chloroform or ethyl acetate for three times. The extracted solutions were combined, and concentrated under vacuum at 40-50° C. with a rotary evaporator. About 20 g of oily crude extract was obtained, which was added into 100 ml of hexane. After stirring for 30 min, solid precipitation appeared. After filtration, about 10 g of solid was obtained, which was completely dissolved in 20 ml of chloroform. The mixture was separated with a silica gel column (200-300 mesh), wherein the ratio of the extract to the silica gel was 1:15. A mixed solvent of chloroform and methanol (9:1) was used as the eluent. The separation process was monitored with thin-layer chromatography. The isolated compound was tested for its antibacterial activity. A compound with significant antibacterial activity was obtained, which was characterized with NMR and MS.

The structure of this compound is shown below:

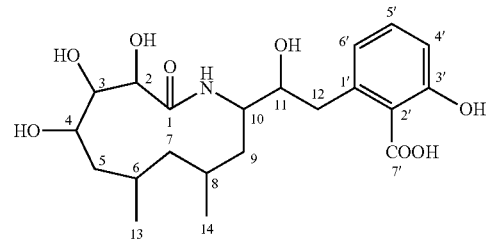 [SMILES: CC1CC(C)CC(C(O)Cc2cccc(O)c2C(=O)O)NC(=O)C(O)C(O)C(O)C1]

Characterization of WH-21091

1D-NMR (13C, 1H) and 2D-NMR (HSQC, DQF-COSY, HMBC) spectra were taken on Bruker WM600 nuclear magnetic resonance spectrometer in $C_5D_5N_5$ as a solvent. ESI-MS spectra were taken with a 70 eV HP 5985 Bgc system. HR-ESI-MS spectra were taken on Kratos MS80 Mass Spectrometer. HPLC and UV analysis were conducted with Waters 2695 HPLC equipped with Waters 996 PDA detector.

From the $^{13}C$-NMR and $^1H$-NMR data listed in Table 1 and the MS data (ESI-MS (m/z): 339; HR-ESI-MS (m/z): 339.4286 ([M-$(H_2O)_5$+4H]$^+$, theoretical value 339.4281)), the formula of the compound is determined to be $C_{21}H_{31}NO_8$, with a molecular weight of 425. Each carbon signal and hydrogen signal was further allocated through HSQC spectra analysis, and the hydrogen-hydrogen correlation DQF-COSY spectrum and carbon-hydrogen correlation HMBC spectrum were further resolved, to finally determine the chemical structure of WH-21091 shown below.

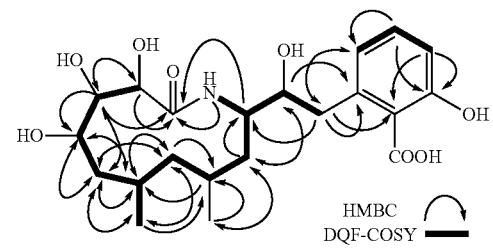

Resolution of DQF-COSY and HMBC of WH-21091

TABLE 1

$^{13}$C-NMR and $^1$H-NMR spectra data of WH-21091

| Serial number of carbon atoms | $^{13}$C-NMR (ppm) | $^1$H-NMR (ppm) |
|---|---|---|
| 1 | 174.0 | |
| 2 | 74.2 | 4.89 (d, 6.0 Hz) |
| 3 | 71.8 | 5.03 (dd, 6.0, 4.5 Hz) |
| 4 | 62.5 | 4.40 (m) |
| 5 | 25.9 | 2.37 (m), 2.22 (m) |
| 6 | 24.9 | 1.85 (m) |

TABLE 1-continued $^{13}$C-NMR and $^1$H-NMR spectra data of WH-21091

| Serial number of carbon atoms | $^{13}$C-NMR (ppm) | $^1$H-NMR (ppm) |
|---|---|---|
| 7 | 45.5 | 3.41 (m) |
| 8 | 24.7 | 1.94 (m) |
| 9 | 39.9 | 1.92 (m), 1.42 (m) |
| 10 | 49.4 | 4.66 (m) |
| 11 | 81.8 | 4.72 (ddd, 14.4, 2.4, 2.4 Hz) |
| 12 | 30.1 | 3.21 (dd, 15.6, 12.6 Hz), 2.95 (dd, 16.8, 3.0 Hz) |
| 13 | 23.4 | 0.84 (d, 7.2 Hz) |
| 14 | 21.8 | 0.92 (d, 6.6 Hz) |
| 1' | 140.8 | |
| 2' | 109.1 | |
| 3' | 162.4 | |
| 4' | 116.0 | 6.96 (d, 8.4 Hz) |
| 5' | 136.5 | 7.35 (t, 7.8 Hz) |
| 6' | 118.7 | 6.62 (d, 7.2 Hz) |
| 7' | 170.0 | |
| CONH | | 8.79 (d, 9.6 Hz) |

Example 2

Antibacterial Activity Test of WH-21091

The following antibacterial activity test of WH-21091 was conducted to illustrate the antibacterial activity of WH-21091. Standard dilution method was adopted, and the measurement was conducted under 35° C. After culturing for 24 hours, the minimum inhibition concentrations (MICs) of WH-21091 were obtained.

Table 2 shows the MICs of WH-21091 on tested microbes. The results indicate that WH-21091 has effective antibacterial effects, especially to some *Staphylococcus* strains which show resistance to antibiotics.

TABLE 2

Antibacterial activities of WH-21091 and erythromycin
(MIC, µg/ml, 24 hr and 48 hr, Medium: trypticase soy broth)

| Bacterial Sample | WH-21091 | erythromycin |
|---|---|---|
| *Escherichia coli* | 4 | 1 |
| *Staphylococcus epidermidis* | 8 | 0.25 |
| *S. aureus* MSRA * | 4 | >32 |
| *Enterococcus faecalis* | 32 | >32 |
| *Streptococcus pyogenes* | 4 | 0.03 |
| *Pseudomonas aeruginosa* | >32 | >32 |

* clinical isolates of methicilllin-resistant strains

Example 3

Test of the Antitumor Activities of WH-21091

Following the method described by Skehan et al. (1990), in vitro antitumor activity tests of WH-21091 on human lung cancer H460, breast cancer MCF-7 and cervix cancer Hela cells were conducted. The results indicate that WH-21091 shows significant antitumor activity on these tumor cells (Table 3).

TABLE 3

Antitumor activities of WH-21091 on tumor cells

| | H460 | MCF-7 | Hela |
|---|---|---|---|
| IC$_{50}$ (µg/ml) | 0.10 | 0.81 | 0.24 |

Although the above description involves many specific features, they are only examples of preferred embodiments, rather than being considered as limitations to the present invention.

REFERENCES

Skehan, et al. (1990) J.-X. Li, G.-H. Chen, J. M. Webster. Nematophin, A novel antimicrobial substance produced by *Xenorhabdus nematophilus* (Enterobactereaceae). *Canadian Journal of Microbiology*, 1997, 43(8): 770-773.

J.-X. Li, K.-J. Hu, and J. M. Webster. Antibiotics from *Xenorhabdus* spp. and *Photorhabdus* spp. (Enterobacteriaceae). *Chemistry of Heterocyclic Compounds*, 1998, 34(11):1331-1339.

S. Park, Y. H. Park, S. Suh, H. S. Kim, I. S. Lee, M. K. Park, C. S. Lee, S. H. Park Unusual cytotoxic phenethylamides from *Xenorhabdus nematophilus*. *Bulletin of the Korean Chemical Society*, 2001, 22(4):372-374.

LIU Wei Jing, YANG Xiu-fen, JIAN Hen, L V Qiu-jun, DONG Jun-xing. The anti-tumor activity of metabolites from *xenorhabdus* and *photorhabdus* in vitro. *Natural Product Research and Development*, 2004, 16(1): 1-6. (in Chinese)

D. Ji, Y. Yi, G. Kang, Y. Choi, P. Kim, N. Baek, Y. Kim. Identification of an antibacterial compound, benzylideneacetone, from *Xenorhabdus nematophila* against major plant-pathogenic bacteria. *FEMS Microbiology Letters*, 2004, 239(2):241-248.

G. Lang, T. Kalvelage, A. Peters, J. Wiese, J. F. Imhoff. Linear and cyclic peptides from the entomopathogenic bacterium *Xenorhabdus nematophilus*. *Journal of Natural Products*, 2008, 71(6):1074-1077.

G. Furgani, E. Böszörményi, A. Fodor, A. Máthé-Fodor, S. Forst, J. S. Hogan, Z. Katona, M. G. Klein, E. Stackebrandt, A. Szentirmai, F. Sztaricskai, S. L. Wolf. *Xenorhabdus* antibiotics: a comparative analysis and potential utility for controlling mastitis caused by bacteria. *Journal of Applied Microbiology*, 2008, 104(3):745-758.

We claim:

1. A compound represented by formula I, pharmaceutically acceptable salt, or tautomer thereof:

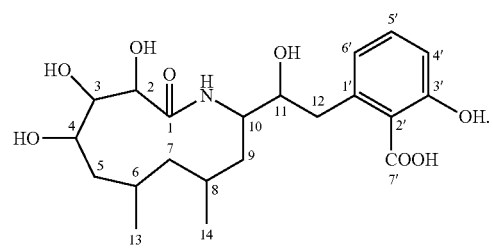

formula I

2. A method for preparing the compound according to claim 1, comprising step of isolating the compound from a secondary metabolic product of microbes selected from the group consisting of: pathogenic *Xenorhabdus* and *Photorhabdus* bacilli which parasitize in *Steinernema* and *Heterorhabditis* nematodes and are symbiotic therewith.

3. The method according to claim 2, wherein the pathogenic bacilli are selected from *Xenorhabdusbovienii, X. nematophila, X. ehlersii* and *X. budapestensis*.

4. A method for preparing the compound according to claim 1, comprising:
1) infecting last-instar larvae of *Galleria mellonella* with nematodes larvae of parasitic bacilli; disinfecting and anatomizing dead larvae; taking lymph and placing on agar medium and culturing under room temperature and darkness; isolating bacilli;
2) culturing of bacilli: the above bacilli are cultured for fermentation, inoculated in a liquid medium containing a carbon source and a nitrogen source, aerobically cultured at 23-27° C. for 24-96 hours, during which the antibacterial activity of the medium is determined at certain intervals until the antibacterial activity of the macrocyclic amide is produced in the medium;
3) preparing WH-21091: after the fermentation culture, the thalli are removed through filtration or centrifuge; the clear solution is adjusted with acetic acid to a pH of 7.0, and extracted with chloroform or ethyl acetate; the extracted solutions are combined, filtered, and concentrated under reduced pressure at 40-50° C.; the obtained extract is separated with column chromatography and eluted with solvent gradient to obtain the macrocyclic amide with antibacterial activities.

5. The method according to claim 4, wherein, when the separation is conducted with column chromatography, the stationary phase is any of silica gel, resin or gel; and when silica gel column chromatography is used, the silica gel is 200-300 mesh silica gel for column chromatography, and the ratio of the extract to the silica gel is 1:15.

6. The method according to claim 4, wherein the strains are cultured in a liquid medium containing a carbon source and a nitrogen source, and a primary culture is conducted firstly, followed by a secondary culture.

7. A pharmaceutical composition comprising the compound, a pharmaceutically acceptable salt, or tautomer thereof according to claim 1 and one or more pharmaceutically acceptable carrier or excipient.

8. The pharmaceutical composition according to claim 7, wherein the pharmaceutical composition is used as an antitumor pharmaceutical composition treating a cancer selected from a group consisting of lung cancer, breast cancer and cervix cancer, or an antibacterial pharmaceutical composition.

9. A method for treating infection caused by bacteria or cancer selected from a group consisting of lung cancer, breast cancer and cervix cancer, comprising administrating a therapeutically effective amount of the compound, a pharmaceutically acceptable salt, ester, or tautomer thereof according to claim 1 to a subject in need thereof.

10. The method according to claim 9, wherein the infection is caused by bacteria of *Escherichia, Staphylococcus, Enterococcus, Streptococcus* or *Pseudomonas*.

* * * * *